United States Patent [19]

Schammel

[11] Patent Number: 4,764,639

[45] Date of Patent: * Aug. 16, 1988

[54] PROCESS FOR THE PRODUCTION OF TRIMELLITIC ACID

[75] Inventor: Wayne P. Schammel, Naperville, Ill.

[73] Assignee: Amoco Corporation, Chicago, Ill.

[*] Notice: The portion of the term of this patent subsequent to Jul. 5, 2005 has been disclaimed.

[21] Appl. No.: 801,564

[22] Filed: Nov. 25, 1985

Related U.S. Application Data

[63] Continuation-in-part of Ser. No. 734,570, May 15, 1985, abandoned.

[51] Int. Cl.$^4$ .......................................... C07C 51/265
[52] U.S. Cl. .................................... 562/416; 562/413
[58] Field of Search ................................ 562/416, 413

[56] References Cited

U.S. PATENT DOCUMENTS

| | | | |
|---|---|---|---|
| 3,161,658 | 12/1964 | Meyer | 562/416 X |
| 3,920,735 | 11/1975 | Wampfler et al. | 562/416 |
| 3,970,696 | 7/1976 | Shigeyasu et al. | 562/416 X |

Primary Examiner—Michael L. Shippen
Attorney, Agent, or Firm—Gunar J. Blumberg; William H. Magidson; Ralph C. Medhurst

[57] ABSTRACT

A process for the manufacture of trimellitic acid for pseudocumene feedstock wherein the amount of cobalt used as catalyst is reduced to the range of about 0.06 to about 0.25 weight percent based on pseudocumene feedstock.

2 Claims, No Drawings

PROCESS FOR THE PRODUCTION OF TRIMELLITIC ACID

BACKGROUND

This is a continuation in part application of Ser. No. 734,570 filed on May 15, 1985, now abandoned.

This invention relates to the liquid-phase oxidation of pseudocumene in the presence of a multi-valent catalyst promoted by a source of bromine wherein the amount of cobalt catalyst added is about 0.06 to about 0.25 weight percent based on pseudocumene feedstock.

The possibility of using liquid-phase instead of vapor-phase oxidation for the preparation of benzene carboxylic acids was first indicated by the disclosure in U.S. Pat. No. 2,245,528 of the catalysis provided by transition or variable valence metals, especially cobalt, in a liquid phase of saturated lower aliphatic acid at temperatures from 100° to 320° C. and pressures to maintain the liquid phase of the aliphatic acid. Such catalysis, according to said patent, was advantageously promoted by the use of a ketone, such as methylethyl ketone, or aldehyde, such as acetaldehyde. Unfortunately, such aldehyde or ketone promoted variable valence metal catalysis was useful only for converting mono-, di-, or trimethylbenzenes to their respective benzene monocarboxylic acids: benzoic, toluic, and dimethyl benzoic acids.

In Canadian Pat. No. 704,424 Baldwin discloses a multistage oxidation system for preparing dicarboxylic acid. Improvements in commercial systems for obtaining maximum yields of aromatic carboxylic acids found in Baldwin's multistage oxidation system are the employment of a bromine-affording substance "in at least the final oxidation stage" and a technique for handling solvent and maintaining the solvent in the final oxidation zone under substantially anhydrous conditions. Baldwin discloses for his multistage oxidation system that a dimethylbenzene, in his example para-xylene, is oxidized by a continuous process wherein a bromine-affording substance is added to the first stage or, if not to the first stage, then "directly into the second stage." This Baldwin patent does not disclose nor suggest a process of staged bromine addition in the oxidation of pseudocumene. Neither does Baldwin suggest the use of the low cobalt to pseudocumene weight ratio. Moreover, the Baldwin patent teaches away from a process of staged bromine addition since it specifically concentrates on a single point of bromine addition in a multi-stage oxidation system.

U.S. Pat. No. 3,920,735 of Wampfler et al. is directed to zirconium-enhanced activity of transition metal-bromine catalysis for oxidation of di- and trimethylbenzene in a liquid phase.

Another reference, U.S. Pat. No. 4,314,073 of Crooks, relates to secondary oxidation in general.

SUMMARY OF THE INVENTION

Pseudocumene is oxidized with molecular oxygen to trimellitic acid, respectively, under liquid-phase conditions in the presence of a catalyst consisting of a source of cobalt, about 0.06 to about 0.25 weight percent based on pseudocumene feedstock, a source of manganese, plus a source of bromine which is calculated to provide a total bromine-to-metals atomic ratio of about 0.4 to about 1.5, at a temperature in the range of about 100° C. to about 250° C.

Pseudocumene (PSC) is oxidized with molecular oxygen to trimellitic acid (TMLA) under liquid-phase conditions in the presence of a catalyst consisting of a source of cobalt, a source of manganese, plus a source of bromine which is calculated to provide a total bromine-to-metals atomic ratio of about 0.4 to about 1.5, at a temperature in the range of about 100° C. to about 250° C., which process comprises conducting the oxidation in two steps so that the amount of bromine added in the first stage is about 10 to about 35 percent of the total bromine added and the remainder is added in the second stage and the total amount of cobalt added is in the range of about 0.06 to about 0.25 weight percent based on pseudocumene feedstock. The preferred range for cobalt is about 0.07 to about 0.19 weight percent based on pseudocumene.

Thus, by charging initially only up to about 35 weight percent of the total bromine charged, our novel process provides fresh bromine to assist in completing the difficult PSC oxidation reaction. This staged bromine addition contributes to an increased yield of TMLA from PSC feedstock as a result of improved selectivity to TMLA.

Our novel process relates to the liquid-phase oxidation of aromatic hydrocarbons having two or more alkyl groups attached to the aromatic ring, using cobalt, manganese and/or other variable-valence metals plus bromine with or without zirconium. The advantage of my process is that I can obtain high yields of TMLA by using about half of the expensive cobalt catalyst.

The source of molecular oxygen for the enhanced oxidation of this invention can vary in $O_2$ content from that of air to oxygen gas. Air is the preferred source of molecular oxygen for oxidations conducted at temperatures of about 100° C. to 250° C. preferably at 100°–150° C. The minimum pressure for such oxidations is that pressure which will maintain a substantial liquid phase of 70–80% of the reaction medium, either neat PSC or PSC and 70–80% of the acetic acid. The acetic acid solvent, when used, can amount to 0.5–4.0 parts on a weight basis per part of the PSC. The PSC and/or acetic acid not in the liquid phase, because of vaporization by heat of reaction, is advantageously condensed and the condensate returned to the oxidation as a means for removing heat and thereby temperature controlling the exothermic oxidation reaction. Such vaporization of PSC and/or acetic acid solvent is also accompanied by vaporization of lower boiling by-product water. When it is desired to take advantage of the benefits of withdrawing acetic acid and water of reaction from the liquid-phase oxidation, as will be hereinafter demonstrated, condensate is not returned to the oxidation.

Our reaction, as applied to PSC, is very difficult and has only been practiced as a batch process in the prior art for the oxidation of PSC because the reaction product, TMLA, is a poison for the catalyst. Batch reactions are successful because high concentrations of the product acid occur only near the end of the oxidation; while in continuous oxidations the product concentration is at a constant high level. Batch oxidations, however, have disadvantages because the concentration of the hydrocarbon near the beginning of the oxidation is high and its rate of oxidation is difficult to control. This leads to a low concentration of dissolved oxygen and increased amounts of hydrocarbon radical reactions producing dimeric, high boiling side products which reduce the yield. Thermally-induced destruction of methyl groups of PSC is also known to occur, thus (or thereby) leading to xylenes which eventually become oxidized to dicarboxylic acid groups, thus leading to yield loss. The use of very small amounts of cobalt versus catalyst are applicable (in process conducted) by batch, continuous or semi-continuous process. In semi-continuous process, we first conduct a semi-continuous oxidation in a manner so that (1) only about one to about two methyl groups on a benzene ring become oxidized to avoid catalyst poisoning, (2) the hydrocarbon concentration is kept low to eliminate much of the radical dimerization reactions, and (3) the temperature is maintained sufficiently low to minimize the destruction of methyl groups. Then, in the second step, we batch oxidize the resultant material from the semi-continuous oxidation so that high concentrations of poisonous product acids occur only near the end of the oxidation.

The total bromine added can be from a single source of bromine, for example, ionic bromine sources (HBr, NaBr, NH$_4$Br, and the like) or from a combined form of bromine, for example, organic bromides such as benzyl bromide, tetrabromoethane and others.

Our invention also includes a process for the oxidation of PSC with molecular oxygen to TMLA under liquid-phase conditions in the presence of a manganese-bromine or cobalt-manganese-bromine catalyst, at a temperature in the range of about 100° C. to about 250° C. For oxidation of PSC, the concentration of catalyst metals per gram mole is as follows for cobalt, about 1 to about 6 milligram atoms, manganese about 1 to about 6 milligram atoms. The concentration of bromine is in a range of about 2 to about 15 milligram atoms per gram mole of PSC.

Our novel process relates to the liquid-phase oxidation of PSC to TMLA using cobalt, manganese, and/or other variable-valence metals plus bromine and when desired, zirconium. A useful catalyst for our process is a zirconium-cobalt-manganese-bromine catalyst wherein the molecular ratio of zirconium to cobalt is about 1 to about 10 to about 1 to about 100 and the oxidation is conducted at a temperature in the range of about 100° C. to about 250° C., which process comprises conducting an oxidation of the pseudocumene so that the first stage is a continuous oxidation, or alternatively is a batch-stage oxidation of PSC so that the concentration of bromine in the first stage is 0 to about 0.5 mole per mole of metals while all the remaining bromine is added during the second stage. The total amount of bromine added is about 50 to about 200 wt. % of the total metal catalysts present. The reaction is completed in a non-continuous process at a temperature of about 140° C. to about 250° C. and, if desired, the solvent and water of reaction is withdrawn during the last 5 to about 20% of the period of the reaction, usually during the last 5 to 20 minutes of the reaction, thus leaving higher TMLA concentrations in the liquid-phase oxidation reactor effluent.

Zirconium can be added to the reaction in any form soluble in the trimethylbenzene being oxidized or in acetic acid when it is being used as reaction solvent. For example, zirconium octanoate or naphthenate can be used with manganese and cobalt octanoates or naphthenates for oxidation of PSC in the absence of reaction solvent and each of Zr, Mn, and Co can be conveniently used as its acetate when PSC is oxidized in the presence of acetic acid solvent. Zirconium is available on a commercial basis as a solution of ZrO$_2$ in acetic acid and, as such, is ideally suited for liquid-phase oxidations using acetic acid as reaction solvent.

In a preferred embodiment, our process for the oxidation of pseudocumene with molecular oxygen to trimellitic acid, under liquid-phase conditions in the presence of a zirconium-cobalt-manganese-bromine catalyst wherein the atomic ratio of zirconium to cobalt is about 1:10 to about 1:100 at a temperature in the range of about 100° C. to about 250° C. and the weight ratio of cobalt to pseudocumene is about 0.07 to 0.19 weight percent, comprises conducting a semi-continuous or batch oxidation of the pseudocumene so that the amount of bromine in the first stage added is about 10 to about 35 percent of the total bromine added and the remainder is added in the second stage which is calculated to provide the total bromine-to-metals atomic ratio of about 0.4 to about 1.5, preferably in the range of about 0.6 to about 1.1 also keeping the concentration of pseudocumene low so that only one methyl group on the average on the benzene ring is converted to a carboxylic acid group thus avoiding the poisoning of the catalyst and completing the reaction in a batch process at a temperature of about 100° C. to about 175° C. to about 150° C. to about 250° C.

For each gram mole of PSC, the concentration of each catalyst metal is as follows, cobalt 1 to 6 milligram atoms, manganese 1 to 6 milligram atoms, zirconium when used 0.1 to 0.5 milligram atoms. The concentration of bromine used is in a range of about 2 to about 15 milligram atoms per gram mole of PSC.

We have established a relationship between the structure of the carboxylic acid and its catalyst-poisoning ability, as shown in Table 1. The experiment described in Table 1 was designed so that the effect of adding specific types of aromatic acids on the rate of oxidation could be obtained. We define a decrease in the rate of oxidation upon addition of an acid as a poisoning effect. We find that at a water concentration of approximately 0.1%, TMLA, hemimellitic acid, and PA decrease the rate of oxidation by precipitating the catalyst metals from solution. Benzoic and phthalic acid do not have such an effect. Another type of poisoning effect is observed at a water concentration of 20% (see Part B of Table 1). Poisoning effects are now observed with phthalic, trimellitic, and hemimellitic acids but the poisoning is not caused by catalyst precipitation. Poisoning without catalyst precipitation occurs when there are two carboxylic acids ortho to each other on the aromatic ring. Catalyst precipitation may occur when there are two carboxylic acids ortho to each other on the aromatic ring but, additionally, one or more acid groups are present. Our novel process is applicable to the oxidation of PSC to TMLA and trimellitic anhydride (TMA).

We show the poisoning effect of trimellitic acid in Table 1. The information in Table 1 was obtained by oxidizing 10.0 ml of pseudocumene in 100 ml of acetic acid using a Co/Mn/Br catalyst [0.500 g and 0.492 g of the cobalt(II) and manganese(II) acetate tetrahydrates and 0.413 g of sodium bromide] at 95° C. and 1.0 atmosphere of air. The rate of oxidation is sufficiently slow so that the concentration of oxidized materials and hence the rate of oxidation remains essentially constant for 2-3 hours. During this time the water and aromatic acid concentration can be instantaneously changed by the appropriate addition into the reaction flask. Oxidation rates ranged from 0 to 7 ml O$_2$/min.

TABLE 1

THE EFFECT OF THE ADDITION OF SELECTED ACIDS TO A CO/MN/BR CATALYZED OXIDATION OF PSEUDOCUMENE

A. INITIAL CONC. OF WATER = 0.1%.

| | | | PERCENT CHANGE IN | | |
|---|---|---|---|---|---|
| RUN NO. | ACID | ACID CONC.,M | OXIDATION RATE | COBALT CONC. | MANGANESE CONC. |
| 1 | benzoic | .95 | +2 | 0 | 0 |
| 2 | o-phthalic | .22 | +33 | 0 | 0 |
| 3 | o-phthalic | .57 | +25 | 0 | 0 |
| 4 | trimellitic | .11 | +2 | −71 | −99 |
| 5 | trimellitic | .30 | −33 | −84 | −100 |
| 6 | trimellitic | .47 | −49 | −85 | −100 |
| 7 | hemimellitic | .037 | −6 | −80 | −90 |
| 8 | hemimellitic | .26 | −99 | −100 | −100 |
| 9 | pyromellitic | .037 | −95 | −98 | −100 |
| 10 | pyromellitic | .074 | −96 | −100 | −100 |

B. INITIAL CONC. OF WATER = 20%

| | | | PERCENT CHANGE IN | | |
|---|---|---|---|---|---|
| EXAMPLE | ACID | ACID CONC.,M | OXIDATION RATE | COBALT CONC. | MANGANESE CONC. |
| 11 | benzoic | .38 | 39 | 0 | 0 |
| 12 | benzoic | .76 | 9 | 0 | 0 |
| 13 | o-phthalic | .19 | −12 | 0 | 0 |
| 14 | o-phthalic | .76 | −97 | 0 | 0 |
| 15 | isophthalic | .12 | 14 | 0 | 0 |
| 16 | trimellitic | .19 | −8 | 0 | 0 |
| 17 | trimellitic | .38 | −61 | 0 | 0 |
| 18 | trimellitic | .57 | −96 | 0 | 0 |
| 19 | hemimellitic | .038 | −77 | 0 | 0 |
| 20 | hemimellitic | .076 | −96 | 0 | 0 |

In the batchwise oxidation of PSC, the exothermic heat of reaction vaporizes some of the liquid solvent which is carried out of the reactor by the process air. The solvent is condensed and returned to the reactor as reflux. This liquid reflux is reheated toward the end of the reaction cycle to ensure temperatures high enough to bring the oxidation to completion. After reaction, the reactor contents are depressurized and TMLA is crystallized out to form a 50–60% solids slurry, this is close to the maximum solids concentration that is pumpable. The solids are filtered out and further processed into final product. The filtrate is disposed of and, therefore, represents a significant yield loss.

A specific, improved oxidation process for the production of TMA from PSC feedstocks comprises the withdrawal of solvent and water of reaction during the last 5 to about 20% of the oxidation reaction time. Where our TMLA recovery process includes a crystallization step, this allows us to increase the crystallizer effluent up to 70–75% solids instead of the 50–60% solids without our novel solvent draw-off process. The recovery of TMLA by the filter increased from about 92.2% to about 97.0% and, where our TMLA recovery process is by dehydration and fractionation of the total oxidation reactor effluent, our novel solvent draw-off process allows a savings of energy.

Another alternate and suitable mode of conduct for the catalytic liquid-phase air oxidation of PSC to TMLA is a staged addition of the bromine component. This improved mode of conduct provides a shorter overall reaction cycle, reduces metals corrosion and contamination of desired crude product while improving the high yields of the desired acid and low production of methylphthalic acids' and formylphthalic acids' impurities which are features of the prior art.

It is particularly desirable to oxidize PSC as completely as possible to TMLA not only to obtain high yields of that acid product in the oxidation effluent but also to provide potential recovery of crude TMLA products with low partial oxidation impurities without extensive oxidation of acetic acid. Low impurity formation is a goal also desirable because TMLA are rather soluble in acetic acid and the methylphthalic acids' and formylphthalic acids' impurities appear to enhance the solubilities of TMLA leading to contamination of the product precipitated from the oxidation effluent, especially a concentrate thereof. Thus, the partial oxidation products in the oxidation effluent have a limiting effect on TMLA precipitations by crystallization from said effluent, making necessary additional processing steps to effect recovery of the remaining TMLA and PMLA solutes in the mother liquor after separation from first crop product crystals. Also, the presence of the impurities require special processing of the total crude TMLA to obtain it in commercially acceptable quality as its intramolecular anhydride.

The present inventive staged addition of bromine for the catalytic liquid-phase air oxidation of PSC to TMLA is conducted using acetic acid reaction medium in the weight ratio to PSC of about 0.5:1.0 to about 4.0:1.0. The metal oxidation catalyst components are cobalt, zirconium, and manganese, or cobalt and manganese. Cobalt concentration based on a gram mole of PSC is in the range of about 1 to about 6, preferably about 2 to about 4, milligram atoms in combination with a source of bromine providing a bromine concentration of about 2.0 to about 15.0, preferably about 2.5 to about 10.0, milligram atoms. The manganese component of the catalyst is at least 10 wt. %, preferably in the range of about 14.0 to about 80.0 wt. % based on the total weight of catalyst metals. The zirconium content of the total metals used is in the range of about 1.0 to about 5.0, preferably about 1.5 to about 4.0, percent by weight of total metals. The cobalt component of the catalyst is in the range of about 15 to about 80 wt. % of the total metals.

When the oxidation of PSC is conducted batchwise, all of the PSC and most (90–99%) of the acetic acid and initial amount of catalyst components are charged at or near oxidation initiation temperature, preferably at about 100° C. to about 165° C., and at a pressure to maintain liquid-phase conditions. Then, pressurized air is injected into the reaction mixture and the reaction temperature is permitted to increase by heat evolved by the oxidation reaction to about 175° C. to about 250° C.

In an advantageous embodiment of our process for the oxidation of PSC with molecular oxygen to TMA under liquid-phase conditions in the presence of a zirconium-cobalt-manganese-bromine catalyst, the atomic ratio of zirconium to cobalt is about 1:10 to about 1:100 and the initial temperature is in the range of about 100° C. to about 220° C. This process comprises conducting an oxidation of the PSC so that in the first stage the amount of bromine added is below about 35 wt. % of the total bromine to be added. Also, this process comprises permitting only partial oxidation of the PSC, thus avoiding the poisoning of the catalyst and completing the reaction in a batch process at a temperature of about 140° C. to about 175° C. to about 150° C. to about 250° C. During the last 5 to about 20 percent of the reaction time, the solvent and water of reaction are withdrawn leaving about 60 to about 75 wt. % solids in the crystallizer effluent.

In a suitable embodiment of our process for the oxidation of PSC with molecular oxygen to TMA under liquid-phase conditions in the presence of a zirconium-cobalt-manganese-bromine catalyst, the molecular ratio of zirconium to cobalt is about 1:10 to about 1:100. This process comprises conducting a semi-continuous or batch oxidation of the PSC so that in the first stage the amount of bromine added is below 20 weight percent of the total bromine to be added. The reaction is completed in a batch process at a temperature of about 100° C. to about 175° C. to about 150° C. to about 250° C.

In an alternate embodiment, our process for the oxidation of PSC with molecular oxygen to TMLA under liquid-phase conditions is conducted in the presence of a cobalt-manganese-bromine catalyst. This process comprises conducting a semi-continuous or batch oxidation of pseudocumene so that in the first stage no bromine is added or not more than 35 percent of the total bromine is added. The reaction is completed in a batch process at a temperature of about 100° C. to about 175° C. to about 150° C. to about 250° C.

It has now been discovered that our novel staged bromine addition process can be further improved by running a semi-continuous oxidation at a partial conversion which is high enough so that the concentration of unreacted hydrocarbon is very low throughout the run, improving product quality and yields. The semi-continuous part of the oxidation is conducted so that the concentration of TMLA is low, usually about 1–5 mole percent, thus preventing premature catalyst deactivation, and the bromine concentration is zero or below 35 percent of the total bromine added. The total bromine added is about 0.5 to about 1.5 moles per mole of cobalt. Thus, the theoretical oxygen uptake is somewhere between 1 and 2.5 moles $O_2$/mole hydrocarbon, with 1.5–2 moles being preferred. Because of side reactions, the actual oxygen uptake may be slightly higher. Also, the semi-continuous oxidation may be run at a low enough temperature, usually about 120° C. to about 200° C., to allow maintenance of an oxygen concentration above 0.5 percent in the vent gas, with 2–8 percent being preferred. After all the hydrocarbon has been pumped in, the oxidation is finished batchwise. In the batchwise step, the temperature of reaction is increased from about 140° C. to about 175° C. to about 150° C. to about 250° C. to compensate for the decreasing reaction rate. In this step, all, or at least 65%, of the bromine used in the catalysts is added.

The following examples illustrate the preferred embodiment of this invention. It will be understood that the examples are for illustrative purposes only and do not purport to be wholly definitive with respect to the conditions and scope of the invention.

EXAMPLE 1

In this Example, data was obtained showing bromine staging in the oxidation of PSC to TMLA. Staging the bromine addition during PSC oxidations produces about a 2.3 mole percent yield improvement over current commercial operations. This yield advantage is due to reduction in high boiling point by-products of about 50 percent and a reduction in burning to carbon oxides of about 15 percent. This Example is for oxidation of PSC with 80 percent bromine staging.

PSC (225 g, 1.875 mole), glacial acetic acid (399 g, 6.53 mole), water (21 g, 1.17 mole), cobalt acetate (1.66 g, 0.0067 mole), manganese acetate (0.45 g, 0.0018 moles), zirconium (0.0136 g, 0.000149 moles) and hydrogen bromide (0.106 g, 0.0013 moles) were charged into a two liter titanium autoclave equipped with a stirrer, internal cooling coil, external electrical heater, and titanium knock-back condenser. After purging the autoclave with nitrogen and pressurizing to 150 psig, the initial charge was heated to a temperature of 320° F. Compressed air was sparged into the autoclave below the liquid level to start the oxidation. Throughout the oxidation a tail-out catalyst mixture containing additional hydrogen bromide was pumped into the autoclave.

The reaction temperature and pressure were increased during the oxidation to a maximum temperature of 410° F. and a maximum pressure of 400 psig. Oxygen and carbon dioxide in the vent gas from the autoclave were measured during oxidation. When the oxygen concentration in the vent gas reached 14.0 percent, the oxidation was terminated by stopping the flow of compressed air into the autoclave and maintaining total pressure with nitrogen. Additional hydrogen bromine used was 0.345 g (0.0043 mole) or 76.5 percent of the total hydrogen bromine (0.451 g). The tailout catalyst solution also added acetic acid (24.6 g, 0.410 mole), water (4.50 g, 0.250 mole), manganese acetate (0.087 g, 0.000356 mole), and zirconium (0.0010 g, 0.000109 mole), to the oxidation mixture.

After reaction, the total reactor effluent and wash were combined, mixed in a blender, and sampled. Samples of about 20 g each were evaporated gently on a steam bath for about 3 hours and then further dried in a vacuum oven at room temperature for 2 days. The dried solid residues were then analyzed by esterification gas chromatography for component analysis. Esterification gas chromatography technique quantifies the low and high boiling by-products.

The product analysis is given in Table 2.

TABLE 2

EXAMPLE 1 - 80% Bromine Staging

| | Wt. % of Solids | Mole % of Pseudocumene |
|---|---|---|
| Trimellitic acid | 93.0 | 90.5 |
| Intermediates | | |
| Dimethyl benzoic acids | 0.09 | 0.13 |
| Aldehydes | 0.22 | 0.30 |
| Methyl dibasic acids | 0.30 | 0.38 |
| Low Boilers | | |
| Phthalic acid | 0.60 | 0.74 |
| Terephthalic acid | 0.43 | 0.53 |
| Isophthalic acid | 0.51 | 0.63 |
| Other low boilers | 0.24 | 0.24 |
| High boiling impurities | 1.20 | 0.89 |
| Mole % $CO_2$ + CO | 5.1 | 5.7 |

COMPARATIVE EXAMPLE A

Comparative Example A was for an oxidation of PSC without bromine staging. PSC (225 g, 1.875 mole), glacial acetic acid (399 g, 6.53 mole), water (21 g, 1.17 mole), cobalt acetate (1.65, 0.0066 mole), manganese acetate (0.50 g, 0.0020 mole), zirconium (0.0090 1 g, 0.000099 mole), and hydrogen bromide (0.619 g, 0.00765 mole) were charged into a two liter titanium autoclave equipped with a stirrer, internal cooling coil, external electrical heater, and titanium knock-back condenser. After purging the autoclave with nitrogen and pressurizing to 150 psig, the initial charge was heated to a temperature of 320° F. Compressed air was sparged into the autoclave below the liquid level to start the oxidation. Throughout the oxidation a tail-out catalyst mixture containing only some additional zirconium and manganese was pumped into the autoclave.

The reaction temperature and pressure were increased during the oxidation to a maximum temperature of 410° F. and a main pressure of 400 psig. Oxygen and carbon dioxide in the vent gas from the autoclave were measured during oxidation. When the oxygen concentration in the vent gas reached 14.0 percent, the oxidation was terminated by stopping the flow of compressed air into the autoclave and maintaining total pressure with nitrogen. No additional hydrogen bromine was used. The tail-out catalyst solution added acetic acid (24.4 g, 0.406 mole), water (4.46 g, 0.248 mole), manganese acetate (0.104 g, 0.000425 mole), and zirconium (0.0123 g, 0.000134 mole) to the oxidation mixture.

TABLE 3

Comparative Example A - Oxidation of Pseudocumene Without Bromine Staging

| | Wt. % of Solids | Mole % of Pseudocumene |
|---|---|---|
| Trimellitic acid | 89.0 | 88.0 |
| Intermediates | | |
| Dimethyl benzoic acids | 0.12 | 0.17 |
| Aldehydes | 0.40 | 0.50 |
| Methyl dibasic acids | 0.27 | 0.34 |
| Low Boilers | | |
| Phthalic acid | 0.76 | 0.95 |
| Terephthalic acid | 0.42 | 0.53 |
| Isophthalic acid | 0.53 | 0.66 |
| Other low boilers | 0.31 | 0.31 |
| High Boilers | 2.38 | 1.80 |
| Mole % $CO_2$ + CO | 6.3 | 6.9 |

Staging the bromine addition during batch pseudocumene oxidations with hydrogen bromine produces a 2.5 mole percent yield advantage over this Comparative Example of batch oxidation.

COMPARATIVE EXAMPLE C AND EXAMPLES 5-8

In Table 4, we have assembled results from several bromine-staging runs and the amount of bromine which is staged ranges from 65 to 100%. In addition, we have included as Comparative Example C a base-case batch run with no bromine staging. Clearly, the wt. % of high boiling impurities decreases as one decreases the amount of bromine which is initially charged to the reactor. At the same time, one can see that the percent TMLA in the product increases.

These data indicate that substantial yield and product quality benefits are obtained by staging the bromine to the reactor. The optimum amount of bromine to be added initially is about 10-20% since this amount will ensure completion of reaction.

TABLE 4

THE EFFECT OF BROMINE STAGING ON THE BATCH OXIDATION OF PSC

| Example | C | 5 | 6 | 7 | 8 |
|---|---|---|---|---|---|
| Run type | Batch Base Case[1] | Batch 65% Br Stage[2] | Batch 80% Br Stage[2] | Batch 90% Br Stage[2] | Batch 100% Br Stage[2] |
| Run time, min. | 74 | 70 | 73 | 75 | 70 |
| PSC burning, mole % $CO_x$ | 5.7 | 6.1 | 6.1 | 6.2 | 5.6 |
| Cake Analysis | | | | | |
| Wt. % OA | 0.80 | 0.77 | 0.76 | 0.65 | 0.71 |
| Wt. % IA +TA | 1.02 | 0.99 | 0.98 | 1.00 | 1.09 |
| Wt. % methyldibasic acids | 0.38 | 0.29 | 0.32 | 0.32 | 0.52 |
| Wt. % high boilers | 2.66 | 1.64 | 1.54 | 1.61 | 1.09 |
| Wt. % TMLA | 91.7 | 93.6 | 94.2 | — | 94.4 |
| Total cake accountability | 97.1 | 97.9 | 98.3 | — | 98.1 |

[1]Control - No bromine staging.
[2]Bromine staging means the percent of total bromine which is not added to the initial reaction mixture, e.g., 65% Br stage indicates that 35% of bromine was added initially and 65% was pumped gradually to the reactor throughout the run.

These reactions are carried out batchwise with an initiation temperature of about 100° C. to about 175° C. About 0-35% of the total bromine to be added is added to the initial reaction mixture. The remaining amount of bromine is added to the tail-out catalyst mixture also containing manganese and zirconium in acetic acid solvent. This tail-out mixture is added slowly to the reaction mixture as the reaction proceeds. Preferably, the tail-out mixture containing most of the bromine is added at a slow, steady rate from the initiation to the end of the run. The primary advantage of bromine staging is that yield and product quality benefits are obtained without having to resort to lower process temperatures or higher air rates.

COMPARATIVE EXAMPLE D AND EXAMPLE 9

In Table 5, we have assembled data showing the effect of bromine staging on TMLA yield and quality. All yields are based on PSC charged to batch oxidations. A batch oxidation reactor was charged with 100 parts by weight of PSC together with 180 parts of 90% acetic acid and an initial catalyst of 0.20 part cobalt, 0.05 part manganese, 0.005 part zirconium promoted with 0.275 part bromine using hydrogen bromide. The initial charge was heated to a temperature of about 160° C. and then air was introduced. After about 20 minutes of oxidation, a tail-out catalyst was added to the oxidizing mixture continuously over about 35 minutes. The total additional catalyst charged in the tail-out catalyst was 0.01 part manganese and 0.005 part zirconium. When the oxygen content of the vent gas coming from the oxidation mixture rapidly increased to above about 14%, the oxidation was terminated. The results of eight such runs were averaged and these averages are reported as Comparative Example D in Table 5.

Again, the batch oxidation reactor was charged with 100 parts by weight of PSC and 180 parts of 90% acetic acid. The initial charge of catalyst added to the reactor was 0.20 part cobalt, 0.05 part manganese, and 0.005 part zirconium, but promoted with only 0.055 part bromine.

Again, the initial charge was heated to a temperature of about 160° C. and then air was introduced. After about 3 minutes of oxidation, a tail-out catalyst was added to the oxidizing mixture continuously over about 52 minutes. The total additional catalyst charged in the tail-out catalyst was again 0.01 part manganese, 0.005 part zirconium and 0.34 part bromine using as a source of bromine tetrabromoethane. When the vent oxygen rapidly increased to over about 14%, the oxidation was terminated. The results of five such runs were averaged and these averages are reported as Example 9 in Table 6.

An average yield of TMLA obtained in eight reactions without using bromine staging is 87.4 mole % based on PSC in the hydrocarbon feed. An average yield of TMLA obtained in five reactions under comparable conditions with bromine staging is 89.5 mole %. The process using bromine staging obtains about a two and one-half percent higher yield than the same process without using bromine staging. Bromine staging reduced intermediate oxidation products by one-third.

TABLE 5
THE EFFECT OF BROMINE STAGING
ON TMLA YIELD AND QUALITY

| | Example | |
|---|---|---|
| | D | 9 |
| Yield[1], mole % | NO BROMINE STAGING[2] | BROMINE STAGING[3] |
| IA +TA | 3.3 | 3.0 |
| Methyldibasic acids | 0.6 | 0.4 |
| High Boilers | 2.0 | 1.4 |
| TMLA | 87.4 | 89.5 |
| $CO_x$ | 7.4 | 7.0 |

[1]Yields are based on PSC charged to batch oxidation.
[2]Yields are averages of eight oxidations.
[3]Yields are averages of five oxidations.

COMPARATIVE EXAMPLES E-H AND EXAMPLES 10-13

One can also use bromine staging in a semi-continuous oxidation rather than batch oxidation to achieve additional benefits.

In Table 6 we have assembled results from several PSC oxidation runs to show the effect of bromine staging on a semi-continuous process for oxidation of PSC conducted at temperatures of 120° C. to 175° C.

TABLE 6
THE EFFECT OF BROMINE STAGING ON SEMI-
CONTINUOUS OXIDATIONS OF PSC AT
TEMPERATURES IN THE RANGE OF
ABOUT 120° C. to 175° C.

| Example | E | 10 | F | 11 |
|---|---|---|---|---|
| Process | Batch | Batch | Semi-continuous | Semi-continuous |
| With Bromine Staging | no | yes | no | yes |

TABLE 6-continued
THE EFFECT OF BROMINE STAGING ON SEMI-
CONTINUOUS OXIDATIONS OF PSC AT
TEMPERATURES IN THE RANGE OF
ABOUT 120° C. to 175° C.

| Example | E | 10 | F | 11 |
|---|---|---|---|---|
| Yield, mole % | | | | |
| IA +TA +OA | 1.8 | 1.9 | 1.4 | 2.1 |
| Methyl dibasic acids | 1.6 | 1.2 | 1.3 | 0.9 |
| High Boilers | 0.6 | 0.5 | 0.4 | 0.4 |
| TMLA | 91.5 | 92.5 | 92.8 | 93.0 |
| $CO_x$ | 4.4 | 3.9 | 4.0 | 3.7 |

The oxidation reaction was conducted as shown in the previous Examples except that low weight percent of cobalt for high weight percent of cobalt is shown. Table 7 clearly demonstates that be reducing the cobalt content up to about 50 percent ho loss of yield is observed.

TABLE 7
Comparison of Low Cobalt and High Cobalt
Catalyst Packages

| mole % Yield | 0.11 wt % Cobalt[1] | 0.20 wt % Cobalt[2] |
|---|---|---|
| TMLA | 89.8 | 89.8 |
| Intermediates | 1.0 | 0.8 |
| Low Boilers | 2.8 | 2.7 |
| High Boilers | 1.2 | 1.2 |
| $CO_x$ | 5.2 | 5.5 |
| Run time, min. | 64 | 65 |

[1]Catalyst Package: Initial; 0.11% Co, .18% Mn, .004% Zr Tailout; 0.05% Mn, .005% Zr 80% Bromine Staging Br/Metals = 1.0
[2]Catalyst Package: Initial; 0.20% Co, 0.084% Mn, .004 .004% Zr Tailout; 0.01% Mn, 0.005% Zr 80% Bromine Staging Br/Metals = 1.0

I claim:

1. A process for the liquid-phase oxidation in a solvent of pseudocumene with molecular oxygen to trimellitic acid, under a sufficient pressure to maintain 70–80% of the solvent and pseudocumene in the liquid-phase in the presence of a source of cobalt, a source of manganses plus a source of bormine with or without a source of zirconium wherein the amount of cobalt present is about 0.06 to about 0.19 weight percent based on pseudocumene feedstock, at a temperature in the range of about 100° C. to about 250° C., which process comprises conducting the oxidation in a two-step process wherein the first oxidation is a semi-continuous oxidation conducted at a temperature of about 100° C. to about 200° C. so that only about one to about two methyl groups on the average on each benzene ring are converted to carboxylic acid groups thus avoiding poisoning the catalyst and completing the oxidation of partially oxidized pseudocumene to trimellitic acid, in a batch oxidation process at a temperature of from about 100° C. to about 250° C. the improvement in combination therewith comprising conducting the staged addition of the bromine component in two stages wherein 10 to about 35 percent by weight of the total bromine is added in the first stage of bromine addition and the remainder is added in the last stage of bromine addition.

2. A process for the liquid-phase oxidation in a solvent of pseudocumene with molecular oxygen to trimellitic acid under a sufficient pressure to maintain 70–80% of the solvent and pseudocumene in the liquid-phase in the presence of a source of cobalt, a source of manganese plus a source of bromine with or without a source of zirconium at a temperature in the range of about 100° C. to about 250° C. the process comprising utilizing about 0.06 to about 0.25 weight percent of cobalt based on pseudocumene feedstock whereby the improvement in combination therewith comprising the addition of bromine in two stages wherein about 10 to about 35 percent by weight of the total bromine is added in the first stage and the remainder is added in the last stage and wherein the temperature in the last stage is about 175° C. to about 250° C., and the temperature in the preceding stage is between about 100° C. and 220° C.

* * * * *

UNITED STATES PATENT OFFICE
CERTIFICATE OF CORRECTION

Patent No. 4,764,639            Dated August 16, 1988

Inventor(s)  Wayne P. Schammel

It is certified that error appears in the above-identified patent and that said Letters Patent are hereby corrected as shown below:

| Col. | Line | |
|---|---|---|
| 9 | 24-25 | "0.0090 1 g, 0.000099" and should read --(0.0090g, 0.000099- |
| 12 | 16 | "ho" and should read --no== |
| 12 | 28 | "Mn, .004 .004% Zr" and should read -- Mn, .004% Zr -- |
| 12 | 36 | "manganses" and should read -- manganese -- |
| 12 | 36 | "bormine" and should read -- bromine -- |

Signed and Sealed this

Thirty-first Day of January, 1989

Attest:

DONALD J. QUIGG

Attesting Officer

Commissioner of Patents and Trademarks